United States Patent [19]

Plattner et al.

[11] B 4,005,138

[45] Jan. 25, 1977

[54] PROCESS FOR THE MANUFACTURE OF SULPHONIC ACID FLUORIDES

[75] Inventors: Eric Plattner, Seltisberg; Christos Comninellis, Prilly, both of Switzerland

[73] Assignee: Ciba-Geigy Corporation, Ardsley, N.Y.

[22] Filed: Sept. 9, 1974

[21] Appl. No.: 504,582

[44] Published under the second Trial Voluntary Protest Program on March 30, 1976 as document No. B 504,582.

[30] Foreign Application Priority Data

Sept. 11, 1973 Switzerland .................... 13025/73

[52] U.S. Cl. ............................................ 260/543 F
[51] Int. Cl.$^2$ ...................................... C07C 143/70
[58] Field of Search .................... 260/543 R, 543 F

[56] References Cited

UNITED STATES PATENTS

| 2,465,951 | 3/1949 | Witte .............................. | 260/543 R |
| 2,465,952 | 3/1949 | Witte et al. ..................... | 260/543 R |
| 3,626,004 | 12/1971 | Guertin ........................... | 260/543 R |

FOREIGN PATENTS OR APPLICATIONS

801,037   9/1958   United Kingdom .......... 260/543 R

OTHER PUBLICATIONS

Merck Index, Seventh Edition, (1960), p. 722.

*Primary Examiner*—John F. Terapane
*Attorney, Agent, or Firm*—Joseph G. Kolodny; Edward McC. Roberts; Prabodh I. Almaula

[57] ABSTRACT

A process for the manufacture of sulphonic acid fluorides of the formula $RSO_2F$, wherein R represents a straight-chain or a branched alkyl or cycloalkyl radical is provided. The process is carried out in liquid hydrogen fluoride and comprises reacting thio compounds of the formula R—S—X, wherein R has the indicated meaning and X is hydrogen or —S—R, with nitrogen dioxide and/or dinitrogen tetroxide. The obtained sulfonic acid fluorides are useful intermediates for the manufacture of a great number of other compounds. By means of electrochemical fluorination they can also be converted into the corresponding perfluoroalkylsulphonic acid fluorides, which can be used as a basis for oil and water repellants.

13 Claims, No Drawings

PROCESS FOR THE MANUFACTURE OF SULPHONIC ACID FLUORIDES

The present invention provides a process for the manufacture of sulphonic acid fluorides of the formula $$RSO_2F,$$

wherein R represents a straight-chain or a branched alkyl or cycloalkyl radical, which comprises reacting thio compounds of the formula $$R-S-X,$$

wherein R has the meaing previously assigned to it and X represents hydrogen or the radical —S—R, with nitrogen dioxide or dinitrogen tetroxide in the presence of liquid hydrogen fluoride.

It is already known to oxidise thiols, for example with hydrogen peroxide, sodium hypochlorite, iodine, copper(II)chloride or with atmospheric oxygen. Dialkyl disulphides are obtained as reaction products according to the following reaction equation:

$$2RSH + I_2 + 2NaOH \rightarrow R-S-S-R + 2NaI + 2H_2O.$$

If oxidation is performed with stronger oxidants, e.g. nitric acid, chromium (VI) oxide, potassium permanganate or bromine, higher oxidised products are obtained, preferably the corresponding sulphonic acids $$RSH + 3 [O] \xrightarrow{HNO_3} RSO_3H.$$

It is also known to oxidise thiols with chlorine or bromine to give the corresponding sulphochlorides or sulphobromides $$RSH + X_2 \xrightarrow{HX\ conc.} RSO_2X \quad X = Cl, Br.$$

The oxidation of organic compounds with molecular oxygen in liquid hydrogen fluoride is described by J. H. Simmons and R. E. McArthur in Industrial and Engineering Chemistry 39, 364 (1947). Benzene can be oxidised under mild conditions to phenol, whereas for example cyclohexane and n-heptane are oxidised under the same conditions to carbon and water.

However, the principle on which the present invention is based, namely the oxidation of organic thio compounds, such as thiols or disulphides, in liquid hydrogen fluoride as reaction medium and nitrogen dioxide or dinitrogen tetroxide as oxidant, is not known.

The process according to the invention can be illustrated by the following reaction scheme:

$$\begin{array}{l}6\ RSH + 2\ NO_2 \rightarrow 3\ RSSR + N_2O + 3\ H_2O \\ \underline{3\ RSSR + 15\ NO_2 + 6\ HF \rightarrow 6\ RSO_2F + 15\ NO + 3\ H_2O} \\ 6\ RSH + 17\ NO_2 + 6\ HF \rightarrow 6\ RSO_2F + N_2O + NO + 6\ H_2O.\end{array}$$

Suitable thiols that can be used as starting compounds in the oxidation according to the invention are straight-chain or branched alkylthiols with 1 to 18, preferably 4 to 14, carbon atoms. Preferred alkylthiols are those with 6 to 12 or 8 to 10 carbon atoms, e.g. n-hexylthiol or n-dodecylthiol or n-octyl-, n-nonyl-, n-decylthiols or tert.octylor or tert. nonylthiols. cycloalkylthiols with 5 or 6 ring carbon atoms, e.g. cyclopentylthiol or cyclohexythiol, are also of interest.

As is apparent from the reaction scheme, in addition to the thiols it is possible to use the corresponding disulphides and optionally also their further oxidation products, for example sulphoxides and sulphones, as starting materials in the process according to the invention. The sulphones cannot be obtained by direct oxidation of thiols with dinitrogen tetroxide; but it is possible to manufacture them by other known processes.

The oxidants, nitrogen oxide and/or dinitrogen tetroxide, are in equilibrium in accordance with the following equation $$N_2O_4 \rightleftarrows 2\ NO_2.$$

Dinitrogen tetroxide becomes solid at −10.3°C and boils under normal pressure at about +21°C.

Hydrogen fluoride is used as reaction medium and as reagent for the sulphonic acid fluoride formation. It has a melting point of −81.1°C and boils at +19.5°C under normal pressure. The hydrogen fluoride used in the reaction has a strength of 50 to 100%, preferably 75 to 100% or, most preferably, 80 to 85%, the remainder up to 100% being water.

The boiling points as function of the composition of the different HF/H₂O mixtures at normal pressure are indicated in the following table:

| HF | Boiling point |
|---|---|
| 70% | 66°C |
| 80% | 47°C |
| 90% | 29°C |

(Ullmann's Enzyklopädie der technischen Chemie 7, 3rd edition 1956)

The possible temperature range for the oxidation at normal pressure is indicated by the physical data of the hydrogen fluoride and of the hydrogen fluoride/water mixtures and of the nitrogen dioxide or dinitrogen tetroxide. Desirably it is between −10°C and +75°C, in particular between +10°C and +40°C or preferably between +10°C and +30°C. If the process is carried out under pressure, then the range between normal pressure and about 10 bar or preferably up to about 4 bar is suitable. If the pressure is indicated as partial pressure of the hydrogen fluoride, it is particularly expedient to carry out the process under 2 to 3 times the partial pressure of the hydrogen fluoride. The reaction time can be from 1 to 10 hours, preferably form about 1 to 5 hours.

If desired, it is also possible to use in addition as reaction medium solvents that are inert to hydrogen fluoride and nitrogen dioxide or dinitrogen tetroxide. Examples of such solvents are perfluorinated or perchlorinated low molecular hydrocarbons, e.g. carbon tetrachloride or trichlorotrifluoroethane.

The molar ratios between the individual raction components can be inferred from the reaction sheme. In actual fact, however, the process is carried out with a large surplus of hydrogen fluoride since this is simultaneously the reaction medium. Further, it is also advantageous to use the nitrogen dioxide (or dinitrogen tetroxide) used as oxidant in a surplus of up to about 30%, based on the stoichiometric amount.

At the conclusion of the reaction, which can be detected by the surplus of brown nitrogen dioxide vapours in the exhaust gases, the reaction mixture forms preferably a two-phase system. The upper phase, which contains the chief portion of the reaction product, is isolated, and the lower phase (principally hydrogen fluoride and impurities) is extracted with an organic solvent in order to obtain further amounts of reaction product. The crude reaction product can be purified by distillation, preferably under reduced pressure.

The concentration of the hydrogen fluoride, which can diminish during the reaction, e.g. through the dilution with water of reaction or also through the removal of hydrogen fluoride together with the exhaust gases, should not fall below 75% if possible, since on the one hand the hydrolysis of the resultant sulphofluoride to sulphonic acid in a more dilute medium than about 80% accelerated rapidly, and on the other hand the reaction vessel is subjected to increased corrosion. Stainless steel is very largely resistant to 75 to 100% hydrogen fluoride at temperatures below 50°C.

Sulphonic acid fluorides can be obtained direct from the corresponding thiols and optionally other starting products by means of the process according to the invention. This was previously not possible since, for example, it was necessary to manufacture the corresponding sulphonic acid chlorides first.

The sulphonic acid fluorides obtained according to the invention are valuable intermediates which, on account of their reactive sulphofluoride group, can be reacted with a great number of other compounds. By means of electrochemical fluorination they can also be converted into the corresponding perfluoroalkylsulphonic acid fluorides, which can be used as a basis for oil and water repellants.

The following Examples illustrate the invention in more detail but do not limit it to what is described therein.

EXAMPLE 1

Manufacture of n-octane-sulphofluoride

A polypropylene flask is used as reaction vessel. The inlet tube for the dinitrogen tetroxide is also of polypropylene or V 4A steel which is coated with polytetrafluoroethylene. The propeller mixer and the thermocouple used for measuring the temperature are also made of V 4A steel.

The exhaust gases (nitrogen oxides) are absorbed by 10% aqueous sodium hydroxide solution. It is also to be borne in mind that hydrogen fluoride and dinitrogen tetroxide are highly toxic skin and respiratory poisons.

350 g of hydrofluoric acid (73%) are put into the reaction vessel and cooled to 5°C to 10°C in an ice bath. With stirring, 250 g of hydrogen fluoride gas (98%) is bubbled in below the surface of the hydrofluoric acid so that the temperature does not exceed +10°C and virtually no hydrogen fluoride gas escapes. 600 g of hydrofluoric acid (83.3%) are obtained. Then 200 g of n-octylthiol (96%; 1.32 moles) are added with stirring. An emulsion forms into which, with good stirring, about 225 g of nitrogen dioxide (4.85 moles, 30% surplus over the theoretical amount) are passed in over the course of 4 to 5 hours in such a manner that the temperature does not rise above 25°C. A surplus of $NO_2$ vapours in the exhaust gases indicates the conclusion of the oxidation. Stirring is subsequently continued for about half an hour. The reaction mixture forms two phases and the lower hydrofluoric acid phase (about 600 g) is isolated. It contains about 570 g of hydrofluoric acid (78.4%) and further constituents and is extracted once with about 500 ml of n-heptane. The extract is distilled at normal pressure. The residue (about 23 g) is combined with the washed crude product and distilled. The upper layer (about 230 g) is washed with 200 ml of water twice, the lower aqueous layer being isolated on each occasion. A total amount of 260 g of crude product (oil; about 87% of crude yield) is obtained.

A distillation flask with an adequate rectifying column (e.g. Vigreux column, 60 cm in length) is filled with the crude product. Different fractions are obtained under a pressure of 20 mbar at increasing bath temperature.

| Fraction | bath °C | distillation temp. °C | yield g | % of theory |
|---|---|---|---|---|
| 1 | up to 140 | up to 120 | 20 (20%)* | 1,5 |
| 2 | 140–170 | 120–125 | 225 (98%) | 85 |
| residue | 170 | — | 15 (5–10%) | 0,5 |

*octane-sulphochloride content determined by gas chromoatography.

The gas chromatography is carried out on a stationary phase of diomataceous earth charged with 14% of phenyl silicone.

| | | |
|---|---|---|
| infra-red spectrum: | 3,43, | 3,52µ  $CH_3(CH_2)_nCH_2-$ |
| | 7,13, | 8,33µ  $-SO_2F$ |
| | 5,86µ | R—CO—R (impurity) |
| nuclear resinance spectrum: | (solvent:deuterochloroform) | |
| | 0,9δ  triplet | $CH_3-CH_2-$ |
| | 1,0–1,8δ  multiplet | $-(CH_2SO_2F$ |
| | 3,3δ  multiplet | $-CH_2SO_2F$ |
| | 2,1δ | $-CH_2CO-$(impurity). |

EXAMPLE 2

The following substances are reacted in accordance with Example 1: 20g (0.125 mole) of tert. nonylthiol and 23g (0.5 mole) of nitrogen dioxide in 125 ml of hydrofluoric acid (80%). The reaction temperature should not exceed 30°C. A brown homogeneous solution is obtained which is extracted with ether. The yield determined by gas chromatography is about 30% of theory (based on tert. nonylthiol).

EXAMPLE 3

The following substances are reacted in accordance with Example 1: 23.2 g (0.2 mole) of cyclohexylthiol and 27 g (0.6 mole) of nitrogen dioxide in 100 ml of hydrofluoric acid (80%). The reaction temperature should not exceed 30°C. A two-phase system forms on conclusion of the reaction. The upper phase is isolated and the lower phase is extracted with benzene. The benzene phase is then distilled and the residual oil is combined with the chief amount of the product.

Crude yield: 19 g of oil.

In addition to impurities, the gas chromatographic analysis yields the following principal products:

| | |
|---|---|
| $C_6H_{11}SH$ | starting product |
| $C_6H_{11}SO_2F$ | end product |
| $C_6H_{11}-S-S-C_6H_{11}$ | disulphide, intermediate product of the oxidation. |

The yield of $C_6H_{11}SO_2F$, based on the disulphide, is about 60 to 70%.

For comparison, the disulphide is manufactured by oxidation of cyclohexylthiol with iodine:

With stirring, iodine is to be added to 22.2 g of cyclohexylthiol in 100 ml of 15% sodium hydroxide solution until the iodine in the reaction mixtures no longer loses colour. The reaction temperature is 20°C.

Yield: 18.2 g (~80% of theory).

This disulphide can also be used for the manufacture of the cyclohexylsulphonic acid fluoride.

We claim:

1. A process for the manufacture of sulphonic acid fluorides of the formula $$R\ SO_2F,$$

wherein R represents a straight-chain or a branched alkyl or cycloalkyl radical, which comprises reacting thio compounds of the formula $$R-S-X,$$

wherein R has the meaning previously assigned to it and X represents hydrogen or the radical —S—R, with nitrogen dioxide or dinitrogen tetroxide in the presence of liquid hydrogen fluoride.

2. A process according to claim 1, which comprises the use of thiols of the formula $$R'-S-H,$$

wherein R' represents alkyl with 1 to 18 carbon atoms or cycloalkyl with 5 or 6 ring carbon atoms.

3. A process according to claim 2, which comprises the use of thiols with 4 to 14 carbon atoms.

4. A process according to claim 3, which comprises the use of thiols with 8 to 10 carbon atoms.

5. A process according to claim 2, which comprises the use of cyclopentylthiol or cyclohexylthiol.

6. A process according to claim 1, wherein the liquid hydrogenfluoride contains up to 50% water.

7. A process according to claim 6, wherein the liquid hydrogenfluoride contains from 15 to 20% water.

8. A process according to claim 1, which comprises the use of nitrogen dioxide or dinitrogen tetroxide in stoichiometric amounts or in a surplus of up to 30%, based on the stoichiometric amount.

9. A process according to claim 1, which comprises carrying out the reaction in a temperature range from −10°C to +75°C.

10. A process according to claim 9, which comprises carrying out the reaction in a temperature range from +10°C to +30°C.

11. A process according to claim 6, wherein the liquid hydrogen fluoride contains up to 25% water.

12. A process according to claim 3, wherein said thiols contain 6 to 12 carbon atoms.

13. A process according to claim 9, wherein said temperature range is from +10°C to +40°C.

* * * * *